United States Patent [19]
Currie

[11] Patent Number: 5,495,854
[45] Date of Patent: Mar. 5, 1996

[54] SELF-TESTING DEVICE FOR MEASURING URINARY FLOW RATES

[76] Inventor: Richard J. Currie, 1238 Hazelwood Dr., Fort Washington, Pa. 19034

[21] Appl. No.: 286,140

[22] Filed: Aug. 5, 1994

[51] Int. Cl.⁶ .................................................... A61B 5/00
[52] U.S. Cl. ................ 128/760; 73/861; 73/226
[58] Field of Search ........................ 128/760, 771; 73/223, 226, 861

[56] References Cited

U.S. PATENT DOCUMENTS

| | | | |
|---|---|---|---|
| 4,099,412 | 7/1978 | Nehrbass | 73/209 |
| 4,238,448 | 12/1980 | Salvador et al. | 422/58 |
| 4,241,017 | 12/1980 | Balistreri et al. | 422/58 |
| 4,409,844 | 10/1983 | Schweiso | 73/861 |
| 4,683,748 | 8/1987 | Carter | 73/226 |
| 4,732,160 | 3/1988 | Ask et al. | 128/760 |
| 4,753,249 | 6/1988 | Muller | 128/771 |
| 5,062,304 | 11/1991 | Van Buskirk et al. | 73/861 |
| 5,176,148 | 1/1993 | Wiest et al. | 128/760 |

FOREIGN PATENT DOCUMENTS 2247626  3/1992  United Kingdom ................ 128/760

*Primary Examiner*—Max Hindenburg
*Attorney, Agent, or Firm*—Howson and Howson

[57] ABSTRACT

A device, a kit of devices, and a method for providing an individual with a means of self-testing for urinary tract obstructions and bladder condition in a simple and inexpensive manner.

16 Claims, 4 Drawing Sheets

SELF-TESTING DEVICE FOR MEASURING URINARY FLOW RATES

FIELD OF THE INVENTION

The present invention relates to a non-invasive screening test for detecting obstructions to the flow of urine exiting the bladder, and more particularly, the present invention relates to a device for providing an individual a means of self-testing for a poor urinary stream which may indicate urinary tract obstructions.

BACKGROUND OF THE INVENTION

There are several illnesses which can cause an obstruction in the flow of urine from the bladder. For instance, a common problem in the aging male is an enlarging prostate gland which obstructs lower tract urinary flow. A poor urinary stream can also result from a weak or diseased bladder.

A helpful tool in the detection of such illnesses is the study of urinary flow rates. While a urinary flow rate study can be used to recognize a symptom, it is non-specific and cannot distinguish between illnesses, for instance between bladder outlet obstruction and impaired bladder contraction. However, the urinary flow rate study is highly accurate in separating individuals having poor urinary streams from individuals having normal urinary flow.

A urinary flow study, also known as uroflowmetry, is the recording of urinary flow rates during the act of micturation. A flow rate of a volume of urine expelled via the urethra per unit of time is expressed in terms of cubic centimeters per second (cc/sec). The flow data provides a peak flow rate, often referred to as (Qmax) and an average flow rate. The peak flow rate is specifically useful since it can identify patients with bladder outlet obstructions. The uroflometry recordings of an individual patient can be compared with those of a normal healthy person's urinary flow. Of course, the flow rates are dependent upon bladder volume, patient's age, outflow obstruction and the degree of abdominal and bladder contractions.

As an example of the usefulness of a urinary flow study, studies have shown that for a urine volume of 200 cc, the average normal healthy male will have a peak flow rate of 19 cc/sec. Studies have also shown that for a urine volume of 200 cc, a peak flow rate of 11 cc/sec or lower would be indicative of an obstructed or poor urinary flow rate in 97% of patients. Therefore, the urinary flow rate study provides an important tool in the detection of such illnesses.

Urinary flow rate studies are also very useful in monitoring the progress of medical treatment. For instance, some illnesses can be treated through the use of drugs. The success, or lack thereof, of the treatment can be monitored by testing the patient's urinary flow rates throughout the period of treatment.

A urinary flow rate study normally requires a patient to make an appointment with a physician and to visit the physician's office to perform the study. The physician will generally have an expensive, complex machine which provides the physician with a printout of the urinary flow rate study after the patient has performed the act of micturation in the appropriate machinery. For instance, U.S. Pat. Nos. 5,176,148; 4,683,748; and 4,732,160 illustrate devices for measuring urinary flow.

The prior art instruments for measuring urinary flow have several drawbacks. One drawback is that the patient must make an appointment with the physician and visit the physician's office in order to perform the test. Therefore, the patient is inconvenienced not only by the expense, but also by having to take the time to visit the physician's office. Another drawback is that the test only represents a single measurement at a single point in time. A single urinary flow measurement may not be representative of the patient's true voiding pattern. In addition, the uncomfortable situation of having observers present while the patient is voiding may also cause the result to be less than representative of the patient's true voiding pattern. The patient in this environment is also more likely to strain his abdominal section or have an intermittent urine flow.

Devices for measuring urinary flow rates which are less complex are also known. For instance, see U.S. Pat. No. 4,099,412. Such devices still require a physician, or nurse, to "eyeball" the flow rate indicia located on the devices while the patient is voiding. These methods still have the drawback of providing only a single test at a single point in time and of placing the patient in a less than comfortable environment.

While the aforementioned devices provide the function of detecting urinary tract obstructions in a somewhat satisfactory manner, there is a need for a device which can be used by an individual at his place of residence to allow the individual to visually observe a good or poor urinary stream. The urinary flow testing device should be inexpensive and simple to use. The device, or a kit having a series of the devices, should allow an individual to test his urinary flow repeatedly over a period of time so that a representative measurement of his true voiding pattern can be obtained. The device being used at one's residence without the presence of other observers should allow the individual to void without the pressure of being in a physician's office with other people present.

OBJECTS OF THE INVENTION

With the foregoing in mind, a primary object of the present invention is to provide a urinary flow testing device which can be used by an individual at his residence without the presence of any observers.

A further object of the present invention is to provide a urinary flow self-testing device which is inexpensive.

A still further object of the present invention is to provide a kit of urinary flow self-testing devices which an individual can use to pre-screen for symptoms of obstructed urinary tracts or to monitor the effect of on-going medical treatment.

Another object of the present invention is to provide a method of testing an individual's urinary flow in a simple manner.

SUMMARY OF THE INVENTION

More specifically, the present invention provides a urinary flow self-testing device which comprises a disposable metering receptacle having an open end into which a patient voids his urine and indicia on the receptacle so that the user of the receptacle can visually detect a good or poor urinary flow.

The receptacle has an outlet port allowing for exit of the urine. The port is sized and located so that as the stream of urine fills the receptacle, the port allows an amount of urine to exit the receptacle at a predetermined rate.

A good urinary stream will result in filling the receptacle at a faster rate than that at which the port allows the urine to exit the receptacle. Thus, when the level of the urine in the receptacle is raised to the level of the indicia, or above, a good urinary flow is indicated. When the level of the urine in the receptacle does not reach the level of the indicia, a poor urinary flow stream is indicated.

The sidewall of the receptacle is tapered in a manner such that the user of the receptacle can look down through the open end of the receptacle and view the level of urine as well as the indicia. Therefore, the receptacle can be used without the presence of another observer.

The present invention also provides a kit of receptacles each having an exit port of a different size. The kit allows a broader range of flow conditions to be tested.

The present invention also provides a method of testing for a good or poor urinary stream. The method includes voiding into a receptacle of the present invention, and visually monitoring the level of the urine in the receptacle relative to indicia located on the receptacle.

BRIEF DESCRIPTION OF THE DRAWINGS

The foregoing and other objects, features and advantages of the present invention should become apparent from the following description when taken in conjunction with the accompanying drawings, in which.

DETAILED DESCRIPTION OF THE PREFERRED EMBODIMENT

Figure 1:
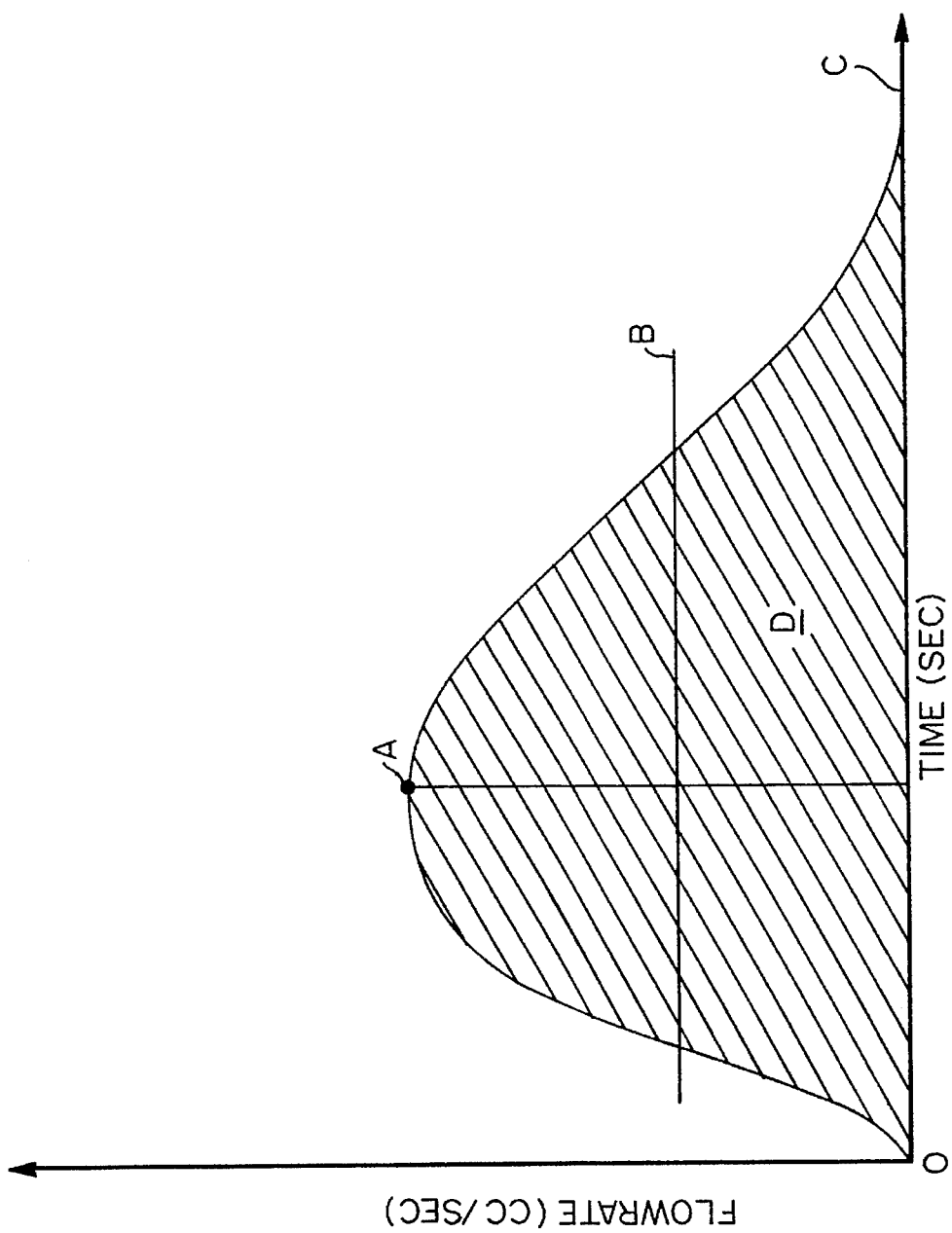
FIG. 1 is a graph schematically illustrating a normal urinary flow rate pattern.

Referring now to the drawings, FIG. 1 illustrates graphically, a urinary flow rate pattern. The graph shows the rate of flow of urine from a patient as a function of time. The area under the curve "D" defines the volume of the voiding. The curve illustrates that after the patient initiates voiding at time "0", the rate of flow increases to a peak, or maximum flow rate, "A". After the maximum flow rate is reached, the flow rate gradually decreases until the voiding is completed at "C". The curve allows the average flow "B" to be calculated.

Information concerning the peak flow rate of an individual is important in the detection of obstructions in the urinary tract and of the weakness of bladders. The average male obtains a maximum flow rate of 19 cc/sec for a voided volume of 200 cc. It has been shown through studies that, in a male, if the peak flow rate is equal to or less than 11 cc/sec for a voided volume of 200 cc, there is a 97% chance that there is some obstruction of the urinary tract.

According to the present invention, a device comprising a receptacle, or cup, 10 (FIG. 2) is provided to allow the user of the cup to visually determine whether or not his urinary flow rate pattern is reflective of a normal healthy individual. The cup 10 also allows the user to visually determine if the user's urinary flow rate pattern is less than that of a normal healthy individual.

The cup 10 has an open end 12 into which a stream of urine can be directed. The cup 10 has a sidewall 14 and bottom wall 16 which allows the cup 10 to collect the voided urine stream. An exit port 18 is located at the center of the bottom wall 16.

The port 18 is precisely sized so that there is an appropriate flow rate of urine exiting the cup 10. The rate at which the fluid exits the cup 10 depends upon the amount or level of the urine held in the cup 10. The higher the level of the urine, the faster the rate of flow exiting the cup through the port 18. The size of the port 18 can be designed to take into account a range of factors, such as age, bladder size, sex, etc, of the patient. The location of the port is preferably in the bottom wall 16, but may be in the sidewall 14.

As a stream of urine is directed through the open end 12 of the cup 10, a portion of the urine will exit through port 18 while a portion of the urine will remain within the confines of the cup 10. The amount of fluid which exits the port 18 is directly dependent on the rate of flow of the stream into the open end 12. If the rate of the stream entering the cup is greater than the rate of the stream exiting the cup through the port 18, then the amount of urine contained within the cup 10 will increase. The level of the urine in the cup will continue to increase until the rate of the stream entering the cup is equal to, or less than, the rate of the urine exiting the cup through the port.

To enable the user to determine flow rates, the sidewall 14 of the cup 10 contains visual indicia 20. The indica 20 is preferably provided by a line extending around the circumference of the cup at a predetermined height above and parallel to the bottom wall 16 of the cup. The indicia 20 may be provided on the outside of the cup 10 if it is of clear plastic; or, it may be provided on the inside if it is opaque. The indicia 20 may be provided either by printing the line, or if desired, by molding it directly into the cup itself. Regardless of how the indicia 20 is applied, the important point is that the indicia 20 be visible by the user when looking vertically downward into the open end 12 of the cup 10.

The indica 20 indicates the minimum level to which the urine should rise if a good urinary stream is present. If the level of urine voided into the cup does not reach the level indicated by the indica 20, then a poor urinary flow rate is present. Other indicia 22 located on sidewall 14 aid in visually determining whether or not the bottom of the cup 10 is being held level while voiding.

Figure 3:
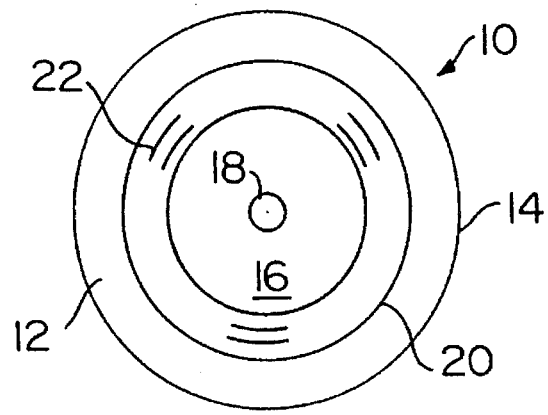
FIG. 3 is a plan view of the receptacle of FIG. 2.

The cup 10 can be used by an individual without requiring the presence of observers. To this end, as best seen in FIG. 3, the sidewall 14 tapers inwardly from its top end to its bottom end. Therefore, when a user views the cup through its open end 12, the user can see most, if not all, the length of the sidewall 14. Since the user can see the sidewall 14, he can also see the indicia 20 located on it. Thus, a male user of the cup 10 can direct his stream into the open end 12 of the cup 10 and visually observe the level of urine relative to the line of indicia 20. This feature allows the user to adopt a more natural voiding stance, thereby avoiding conditions that may not be representative of his true normal voiding pattern. This feature also precludes the need for a second individual to "eyeball" the cup from the side as the user voids into the cup 10, thereby minimizing errors that may be induced by the uneasiness of the user voiding in the presence of another person.

Cup 10 provides a simple screening means for enabling an individual to determine whether or not he has a urinary flow rate problem. The cup 10 is simple to manufacture and therefore is inexpensive. The cup 10 can be used once and discarded, allowing for the use of a sanitary cup each time. The cup 10 can be made of disposable plastic, rigid paper, or like recyclable materials. While the design of cup 10 shown in FIGS. 2 and 3 resembles that the of an ordinary cup, any design can be used provided the following variables are considered: the size of the exit port and its relation to the possible fluid levels within the cup; the volume of the cup; the placement of the indicia on the cup; the relation between the indicia on the cup and the volume of the cup; and the ability for the indicia to be viewed from a position above the opening of the cup.

Figure 2:
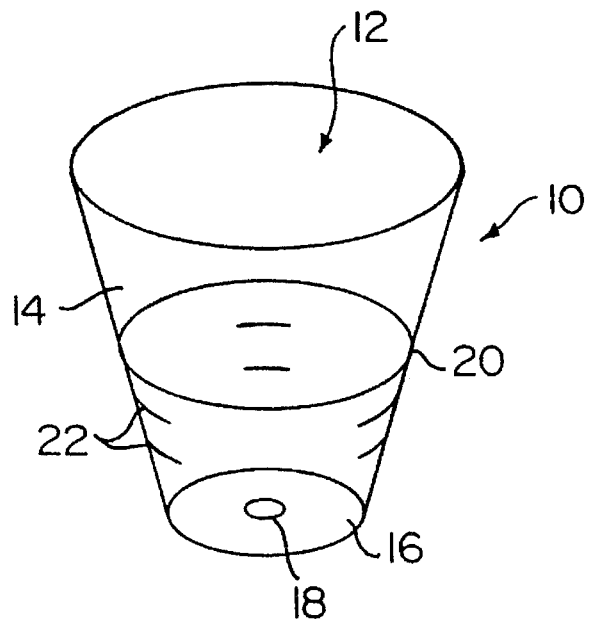
FIG. 2 is a perspective view of one embodiment of a receptacle of the present invention.

By way of example only, and not by way of limitation, a preferred cup 10, as shown in FIGS. 2 and 3, contains ten fluid ounces. The cup measures four inches in height. The base of the cup is circular and two inches in diameter while the open end of the cup is three inches in diameter. The sidewall of the cup has a constant inward taper from the upper open end to the base. An exit port having a circular shape is located at the center of the base. The exit port is 5/32 inches in diameter. The indicia 20 is located 1⅛ inches above the bottom of the cup and extends circumferentially and continuously around the cup sidewall. These dimensional relations ensure that if a user is capable of voiding at a rate such that the level of urine in the cup rises to the line of indicia 20, or above, then the stream of urine flow into the cup is at least 11 cc/sec, provided the voided volume was greater than, or equal to, 200 cc. If the user voided 200 cc or more and did not reach a level of urine at or above the line of indicia 20, then tests have shown that the user has a 97% chance of having a poor urine flow.

The receptacle can be used by an individual to self-screen and decide if he should consult a physician concerning a urinary tract obstruction or weak or diseased bladder condition. Alternatively, the use of the cup can be utilized to check the progress of treatment by a physician concerning many urinary tract problems.

For certain individuals, depending upon age, physical condition, treatment regimens, or the like, it may be necessary to provide a kit of cups to enable a broader range of flow conditions to be tested.

For instance, if an individual is capable of voiding at a rate that rises above the line of indicia 20 with cup "A" as described above, and therefore has a stream flow rate of over 11 cc/sec, the individual may want more detailed flow information. Therefore, a second cup, "B" having the same specifications as "A", but with an exit port 7/32 inch in diameter and a line of indicia 20, 1¼ inches from the bottom of the cup may be used. The use of "B" cup would indicate to the user that if the voided urine has a volume of at least 200 cc, and the level of the urine reaches the line of indicia 20, then the individual will know that he has at least a flow rate of 19 cc/sec. However, if the individual's flow rate is such that the urine level does not reach the second line, then the individual will know that he has a stream flow rate of less than 19 cc/sec, but greater than 11 cc/sec, this lower rate having been determined by using cup "A" of the kit.

It should become apparent that by supplying a user with a kit containing a variety of different cups, either having different volumes, exit port diameters, or levels of indicia 20, an individual can self-determine a good or poor urinary stream, or monitor whether his flow rate is increasing or decreasing over a period of time.

The present invention also provides a method of testing for urinary tract obstructions and weak bladders. In this method, an individual must first obtain a receptacle as described herein and hold it with its bottom as level as possible. The individual voids into the open end of the receptacle and visually monitors the level of voided urine relative to the indica located on the receptacle. Since the receptacle is tapered, the individual can monitor the level of urine relative to the indicia by looking directly downward through the open end of the receptacle. If the level of urine reaches the indicia 20, a good urinary stream is indicated.

Figure 4:
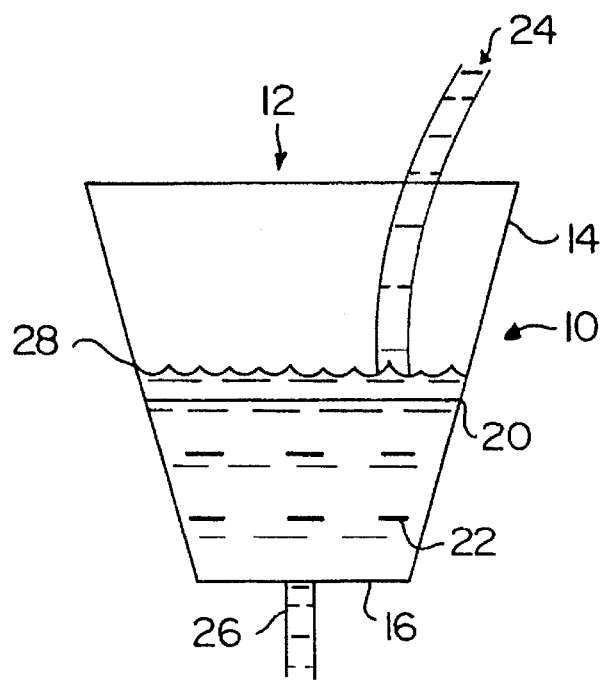
FIG. 4 is an elevational view of a receptacle in use with a good urinary stream.
Figure 5:
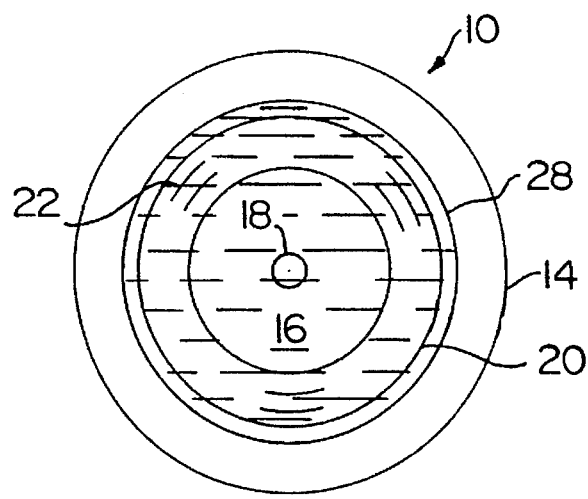
FIG. 5 is a plan view of FIG. 4.

A good urinary stream is diagrammatically shown in FIG. 4 and FIG. 5. As seen therein, the urinary stream 24 enters the open end 12 of cup 10. The voided urine contained in cup 10 rises to the level 28. The level of urine 28 is a function of the rate of flow of urinary stream 24, the rate of urine 26 exiting via port 18, and the volume of urine voided. Since the level of urine 28 is above indica 20, a good urinary stream without urinary tract obstructions is indicated. FIG. 5 illustrates the user's view looking downward through the open end 12 of the cup 10.

Figure 6:
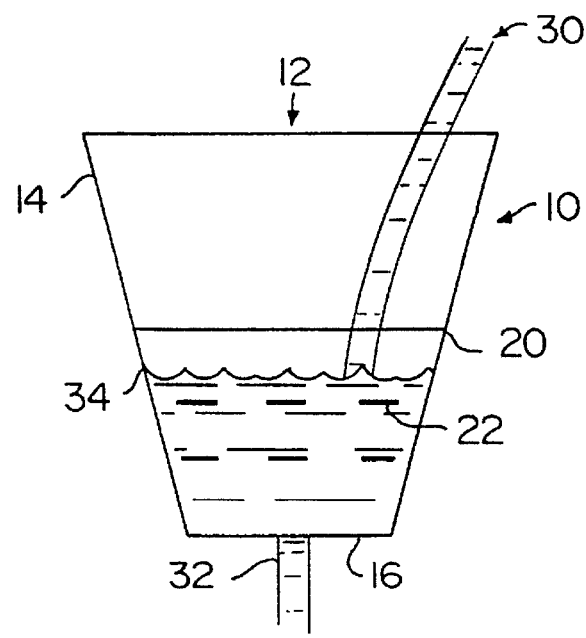
FIG. 6 is an elevational view of a receptacle in use with a poor urinary stream.
Figure 7:
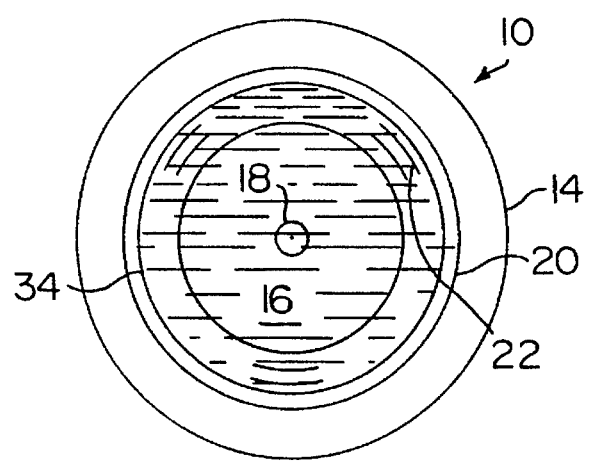
FIG. 7 is a plan view of FIG. 6.

A poor urinary stream is shown diagrammatically in FIG. 6 and FIG. 7. As seen there, urinary stream 30 enters the open end 12 of cup 10. Because the urinary stream 30 is not strong enough to offset the rate at which urine 32 exits the cup, the level of urine 34 does not reach indicia 20. The voided urine contained in cup 10 only reaches to level 34. Therefore, since the level of urine 34 never reaches indicia 20, a poor urinary stream with possible urinary tract obstruction is indicated. FIG. 7 illustrates the user's view looking downward through the open end 12 of the cup 10.

While various modifications can be made, it should be apparent that the present invention provides a device and method by which urinary tract obstructions can be detected in a simple, inexpensive, and convenient manner.

I claim:

1. A device for non-invasive detection of urinary tract obstructions and bladder condition, comprising:

a receptacle having a sidewall and a base capable of temporarily confining a volume of urine and allowing a level of said urine to be visually observed;

said receptacle having an open end for receiving a stream of said urine;

said receptacle having a port at said base allowing a quantity of said urine to exit at a predetermined rate; and flow-level indicia provided on said sidewall of said receptacle to allow visual relative comparison of said indicia with said level of urine;

said sidewall being continuous between said base and said flow-level indicia;

whereby a level of urine reaching the flow-level indicia indicates a satisfactory urinary flow rate.

2. A device according to claim 1, wherein said sidewall tapers inwardly from said open end to said base, and said indicia is provided on said sidewall at a location permitting visual observation through said open end.

3. A device according to claim 2, wherein said indicia is located on said sidewall at a predetermined level above said base.

4. A device according to claim 3, wherein said indicia is visually perceptible on the inside of the sidewall.

5. A device according to claim 4, wherein said indicia comprises a circumferential line on said sidewall parallel to said base.

6. A device according to claim 5, wherein said indicia includes additional markings located on said sidewall to aid in monitoring the rise in level of urine.

7. A device according to claim 6, wherein said port is circular in shape and has a diameter of between about $5/32$ and $7/32$ inches, and wherein said indicia is located between about $1\frac{1}{8}$ and $1\frac{1}{4}$ inches from said base.

8. A kit of receptacles for use in self-screening urinary flow rates to detect urinary tract obstructions and bladder condition, comprising:
- a plurality of receptacles, each receptacle capable of confining a volume of urine and allowing a level of urine to be visually observed;
- each of said receptacles having an open end for receiving a stream of urine;
- each of said receptacles having a port allowing a quantity of urine to exit from said receptacle at a predetermined rate;
- each of said receptacles having indicia thereon allowing visual relative comparison of said indicia with said level of urine; and
- at least two receptacles in said kit being characterized by having exit ports of different sizes; whereby a level of urine reaching said indicia indicates a satisfactory urinary flow rate.

9. A kit according to claim 8, wherein each of said receptacles is identical in overall configuration to the other, except for exit port size.

10. A kit according to claim 9, wherein said at least two said receptacles are marked to indicate their differences in flow rate measurements.

11. A kit according to claim 10, wherein one of said at least two receptacles indicates a higher level of satisfactory urine flow without obstruction.

12. A kit according to claim 11, wherein said port of said at least one of said two receptacles is larger than in said other receptacle.

13. A kit according to claim 11, wherein said indicia of at least one of said two receptacles is located at a higher level on said receptacle than said other of said two receptacles.

14. A method for non-invasive detection of urinary tract obstructions and bladder condition, comprising the steps of:
- obtaining a receptacle having a sidewall, a base, an open end, an exit port at said base affording discharge of urine at a predetermined rate, and flow-level indicia on said sidewall, said sidewall being continuous between said base and said indicia;
- voiding a stream of urine into said open end of said receptacle; and
- monitoring visually the level of urine flowing into said receptacle relative to said flow-level indicia;

whereby the level of urine relative to said flow-level indicia indicates urinary flow rate.

15. A method according to claim 14, wherein said sidewall is tapered inwardly from said open end, and voiding occurs while looking into the cup directly downward into the open end.

16. A method according to claim 14, further comprising the steps of obtaining a second receptacle having an exit port of a size different from said first-mentioned receptacle, and repeating said voiding and monitoring steps.

* * * * *